(12) United States Patent
Coates et al.

(10) Patent No.: US 7,723,256 B2
(45) Date of Patent: May 25, 2010

(54) POLYCARBONATES MADE USING HIGHLY SELECTIVE CATALYSTS

(75) Inventors: Geoffrey W. Coates, Ithaca, NY (US); Zengquan Qin, Copley, OH (US); Claire Tova Cohen, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/976,800

(22) Filed: Oct. 29, 2007

(65) Prior Publication Data

US 2008/0108499 A1 May 8, 2008

Related U.S. Application Data

(62) Division of application No. 11/244,231, filed on Oct. 6, 2005, now Pat. No. 7,304,172.

(60) Provisional application No. 60/616,630, filed on Oct. 8, 2004.

(51) Int. Cl.
*B01J 31/18* (2006.01)
*B01J 31/00* (2006.01)
*C08G 67/02* (2006.01)

(52) U.S. Cl. .................. 502/167; 528/392
(58) Field of Classification Search .................. 502/167
See application file for complete search history.

(56) References Cited

U.S. PATENT DOCUMENTS

| | | | |
|---|---|---|---|
| 4,066,630 A | 1/1978 | Dixon et al. | |
| 5,354,499 A | 10/1994 | Elliott | |
| 6,713,593 B2 | 3/2004 | Ree et al. | |
| 6,720,434 B2 * | 4/2004 | Kim et al. | 549/523 |
| 6,870,004 B1 * | 3/2005 | Nguyen et al. | 525/88 |
| 7,157,398 B2 * | 1/2007 | Schottek et al. | 502/102 |
| 2005/0240032 A1 * | 10/2005 | Luinstra et al. | 549/263 |
| 2007/0225524 A1 * | 9/2007 | Schanen et al. | 564/12 |
| 2007/0255039 A1 * | 11/2007 | Coates et al. | 528/392 |

FOREIGN PATENT DOCUMENTS

WO WO0009463(A1) 2/2000

OTHER PUBLICATIONS

Darensbourg et al, Inorg. Chem., 1996, 35, 2682-2684.*
Lu, X.-B., et al., J. Am. Chem. Soc., "Design of Highly Active Binary Catalyst Systems for $CO_2$/Epoxide Copolymerization: Polymer Selectivity, Enantioselectivity, and Stereochemistry Control", published on Web Jan. 12, 2006.

Qin, Z., et al., "Cobalt-Based Complexes for the Copolymerization of Propylene Oxide and $CO_2$: Active and Selective Catalysts for Polycarbonate Synthesis", Angew. Chem. Int. Ed. 42, 5484-5487 (published online Oct. 20, 2003) and supporting information.
Lu, X.-B., et al., "Highly Active, Binary Catalyst Systems for the Alternating Copolymerization of $CO_2$ and Epoxides under Mild Conditions", Angew. Chem. Int. Ed. 43, 3574-3577 (Jul. 5, 2004).
Paddock, R. L., et al., "Alternating Copolymerization of $CO_2$ and Propylene Oxide Catalyzed by $Co^{III}$(salen)/Lewis Base", Macromolecules 38, 6251-6253 (Published online Jun. 30, 2005).
Chisholm et al., "Poly(propylene carbonate). 1. More about Poly(propylene carbonate) Formed from the Copolymerization of Propylene Oxide and Carbon Dioxide Employing a Zinc Glutarate Catalyst" *Macromolecules* 35:6494-6504 (2002).
Darensbourg et al., "Mechanistic Aspects of the Copolymerization Reaction of Carbon Dioxide and Epoxides, Using a Chiral Salen Chromium Chloride Catalyst" *J. Am. Chem. Soc.* 124:6335-6342 (2002).
Darensbourg et al., "Comparative Kinetic Studies of the Copolymerization of Cyclohexene Oxide and Propylene Oxide with Carbon Dioxide in the Presence of Chromium Salen Derivatives. In Situ FTIR Measurements of Copolymer vs Cyclic Carbonate Production" *J. Am. Chem. Soc.* 125:7586-7591 (2003).
Lednor et al., "Copolymerization of Propene Oxide with Carbon Dioxide: Aselective Incorporation of Propene Oxide into the Polycarbonate Chains, determined by 100 MHz $^{13}$C N.M.R. Spectroscopy" *J. Chem. Soc., Chem. Commun.* 598-599 (1985).
Lu et al., "Asymmetric Catalysis with $CO_2$: Direct Synthesis of Optically Active Propylene Carbonate from Racemic Epoxides" *J. Am. Chem. Soc.* 126:3732-3733 (2004).

* cited by examiner

*Primary Examiner*—Stanley Silverman
*Assistant Examiner*—Yun Qian
(74) *Attorney, Agent, or Firm*—Choate, Hall & Stewart LLP; Charles E. Lyon; John P. Rearick

(57) ABSTRACT

Poly(propylene carbonates) are prepared from propylene oxide and $CO_2$ with less than 10% cyclic propylene carbonate by product using cobalt based catalysts of structure

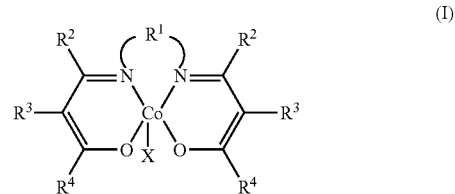

(I)

preferably in combination with salt cocatalyst, very preferably cocatalyst where the cation is $PPN^+$ and the anion is $Cl^-$ or $OBzF_5^-$. Novel products include poly(propylene carbonates) having a stereoregularity greater than 90% and/or a regioregularity of greater than 90%.

28 Claims, No Drawings

POLYCARBONATES MADE USING HIGHLY SELECTIVE CATALYSTS

CROSS-REFERENCE TO RELATED APPLICATIONS

This application is a division of U.S. application Ser. No. 11/244,231, filed Oct. 6, 2005 which claims the benefit of U.S. Provisional Application No. 60/616,630, filed Oct. 8, 2004, the whole of both of which are incorporated herein by reference.

The invention was made at least in part with U.S. Government support under National Science Foundation Contract No. DMR-0079992. The U.S. Government has certain rights in the invention.

TECHNICAL FIELD

The invention is directed at high selectivity cobalt containing catalysts for producing poly(alkylene carbonates) from alkylene oxide and carbon dioxide, to a process for producing polycarbonates using the catalysts and to polycarbonates produced thereby.

BACKGROUND OF THE INVENTION

The generalized mechanism of $CO_2$/epoxide copolymerization involves two steps, namely epoxide ring opening by a metal carbonate followed by $CO_2$ insertion into a metal alkoxide. When aliphatic epoxides such as propylene oxide are used, a common side-product is the cyclic carbonate. The most active catalysts, namely [Zn(BDI)OAc] and [Cr(salph)Cl]/DMAP, reported to date, produce 10-30% of unwanted cyclic propylene carbonate (CPC) by-product, under optimized conditions.

SUMMARY OF THE INVENTION

It has been discovered herein that catalysts of sufficient activity for commercial production and which have selectivity of greater than 90:1 poly(propylene carbonate) (PPC) to CPC, often greater than 99:1 PPC to CPC, are enantiomerically pure cobalt catalysts, e.g., (salen)Co$^{III}$(X) complexes and the like.

In a first embodiment herein, there are provided cobalt containing compounds useful as catalysts for $CO_2$/$C_2$-$C_{10}$ alkylene oxide copolymerization with little or no cyclic alkylene carbonate by-product. These compounds have the structural formula:

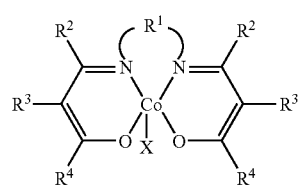

(I)

where $R^1$ is a hydrocarbon bridge which may be substituted with $C_1$-$C_{20}$ alkyl, $C_1$-$C_{20}$ alkoxy, halogen (e.g., Cl, Br, I), nitro, cyano or amine; where $R^2$, $R^3$ and $R^4$ can be the same or different and are selected from the group consisting of H, $C_1$-$C_{20}$ alkyl, $C_6$-$C_{20}$ aryl, and $C_1$-$C_{20}$ fluorocarbon and where $R^2$ and $R^3$ or $R^3$ and $R^4$ can form a ring which can be substituted with H, $C_1$-$C_{20}$ alkyl, $C_6$-$C_{20}$ aryl, $C_1$-$C_{20}$ alkyl $C_6$-$C_{20}$ aryl substituted with $C_1$-$C_{20}$ alkyl, $C_1$-$C_{20}$ alkoxy, phenoxy, $C_1$-$C_{20}$ carboxylate, $C_1$-$C_{20}$ acyl, amino, $C_1$-$C_{20}$ fluoroalkyl, cyano, nitro or halogen (e.g., Cl, Br, D or a solid support and where X is any nucleophile which can ring open an epoxide.

The term "solid support" as used herein refers to a soluble or insoluble polymeric structure, such as crosslinked polystyrene, or an inorganic structure, e.g., of silica or alumina.

The cases of X being nitro-substituted phenoxide are excluded when $R^1$ is 1,2-cyclohexanediyl to avoid disclosure in Lu, X-B, et al, Angew. Chem. Int. Ed 43, 3574-3577 (2004).

For the structure where X is Br, $R^1$ is ethyl and $R^3$ and $R^4$ form a phenyl ring, the case is excluded where the substituents on the phenyl ring on carbons which are not also part of another ring, are all H, because this compound has been found to be inactive in producing poly(propylene carbonate).

For the structure where X is Br, $R^1$ is 1,2-cyclohexanediyl and $R^3$ and $R^4$ form a phenyl ring, the case is excluded where substituents on carbon on the phenyl ring which is not also part of another ring and is closest to O is not H, because this compound has been found to be inactive in producing poly (propylene carbonate).

In another embodiment, denoted the second embodiment, there is provided a catalyst system for use in catalyzing the copolymerization of $C_2$-$C_{10}$ alkylene oxide, and carbon dioxide to produce poly($C_2$-$C_{10}$ alkylene carbonate), e.g., poly (propylene carbonate), with less than 10% cyclic alkylene carbonate, e.g., cyclic propylene carbonate, by-product, comprising compound of the first embodiment as catalyst and a salt cocatalyst which is bulky and non-coordinating where the cation is any bulky cation, e.g., a phosphorus and/or nitrogen based cation, e.g., $[R_4N]^+$, $[R_4P]^+$, $[R_3P=N=PR_3]^+$ or $[P[NR_3]_3]^{3+}$ where R is $C_1$-$C_{20}$ alkyl or $C_6$-$C_{20}$ aryl or a solid support, where the unsupported cation or the ionic portion of a supported cation has a molecular weight ranging, for example, from 750 g/mol to 2000 g/mol, and the anion is a nucleophile which can ring open an epoxide, and the R groups can be the same or different.

In another embodiment, denoted the third embodiment, there is provided a method for preparing poly($C_2$-$C_{10}$ alkylene carbonate)s, e.g., poly(propylene carbonate), by copolymerization of $C_2$-$C_{10}$ alkylene oxide, e.g., propylene oxide, and carbon dioxide with less than 10% cyclic $C_2$-$C_{10}$ alkylene carbonate, e.g. cyclic propylene carbonate, by-product, comprising the step of reacting $C_2$-$C_{10}$ alkylene oxide and carbon dioxide at a $CO_2$ pressure ranging from 1 to 1,000 psi, a reaction temperature of 0 to 150° C. and a reaction time of 0.1 to 50 hours, in the presence of a catalyst which is compound of the first embodiment at alkylene oxide to catalyst ratio on a cobalt basis ranging from 200:1 to 100,000:1

In another embodiment, denoted the fourth embodiment, there is provided a method for preparing poly($C_2$-$C_{10}$ alkylene carbonate), e.g., poly(propylene carbonate), with less than 10% cyclic alkylene carbonate, e.g., cyclic propylene carbonate by-product, comprising the step of reacting $C_2$-$C_{10}$ alkylene oxide, e.g., propylene oxide, and $CO_2$ at a $CO_2$ pressure ranging from 1 psi to 300 psi, a reaction temperature of 0 to 100° C., and a reaction time of 0.1 to 50 hours, e.g., 0.5 to 4 hours, in the presence of the catalyst system of the second embodiment, where the ratio of alkylene oxide to cocatalyst to catalyst ranges from 500-100,000:0.5-1.5:0.5-1.5

In another embodiment, denoted the fifth embodiment, there is provided poly(propylene carbonate) of $M_n$ ranging from 500 to 1,000,000 g/mol and polydispersity index (PDI) ranging from 1.05 to 5.0, e.g., 1.05 to 1.30, with greater than 90% head-to-tail linkages. In one case, the polymer has random stereochemistry. In another case, more than 90% of adjacent stereocenters have the same relative stereochemistry (isotactic).

In another embodiment, denoted the sixth embodiment, there is provided poly(propylene carbonate) of $M_n$ ranging from 500 to 1,000,000 g/mol and PDI ranging from 1.05 to 5.0, e.g., 1.05 to 1.30, where greater than 90% of the stereocenters are of the same stereochemistry.

The molecular weight of the polycarbonate can be increased within the stated range by longer polymerization times. The molecular weight of the polycarbonate can be decreased within the range by the addition of chain transfer agents in the form of carboxylic acids (e.g. pentafluorobenzoic acid), alcohols (e.g. methanol), dicarboxylic acids, diols, poly acids, polyols, and their deprotonated forms (e.g., sodium pentafluorobenzoate) and other additives known to promote chain transfer. The polymerization can also be conducted in solvent.

$M_n$ and PDI here are determined by gel permeation chromatography in tetrahydrofuran at 40° C., calibrated with polystyrene standards.

DETAILED DESCRIPTION

In an example of the first embodiment

(II)

in the structure (I) is selected from the group consisting of:

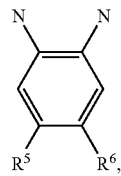
(III)

(R,R) or (S,S)
or rac
n = 0,1
(IV)

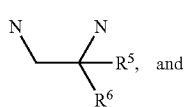
(V)

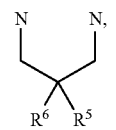
(VI)

where $R^5$ and $R^6$ can be the same or different and are H, $C_1$-$C_{20}$ alkyl, $C_6$-$C_{20}$ aryl, halogen (e.g., F, Cl, Br, I), nitro, cyano, $C_1$-$C_{20}$ alkoxy or amine.

X in the formula (I) can be selected, for example, from the group consisting of $C_1$-$C_{20}$ alkyl, halogen (e.g., Cl, Br, I), $C_1$-$C_{20}$ amido, cyano, azide, $C_1$-$C_{20}$ alkyl carboxylate, $C_6$-$C_{20}$ aryl carboxylate, $C_1$-$C_{20}$ alkoxide and phenoxide.

In one case, the compounds have the structure:

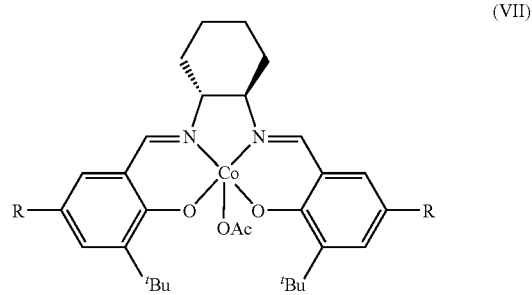
(VII)

where R is selected from the group consisting of Br, H and $^t$Bu.

In an overlapping case, the compounds have the structure

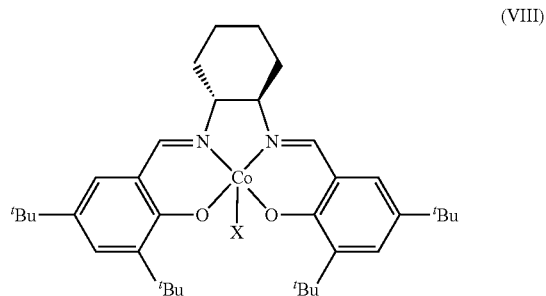
(VIII)

where X is Br, Cl, I, OAc, $OBzCF_3$ (p-trifluoromethylbenzoate) or $OBzF_5$ where $OBzF_5$ is 2,3,4,5,6-pentafluorobenzoate. The compound of structure (VIII) where X is $OBzF_5$ is novel.

In still another case, the compounds have the structure

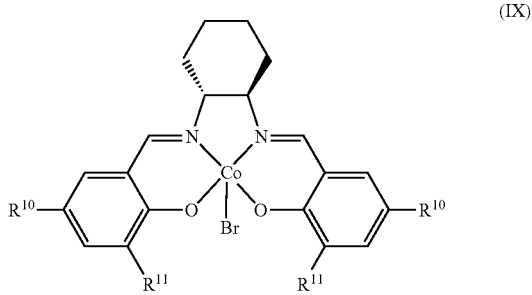
(IX)

where $R^{11}$ is $^t$Bu and $R^{10}$ is selected from the group consisting of H, Br and OMe; $R^{11}$ is Me and $R^{10}$ is H; or $R^{11}$ is $CPh(CH_3)_2$ and $R^{10}$ is $CPh(CH_3)_2$. The compounds are novel.

In still another case, the compound has the structure

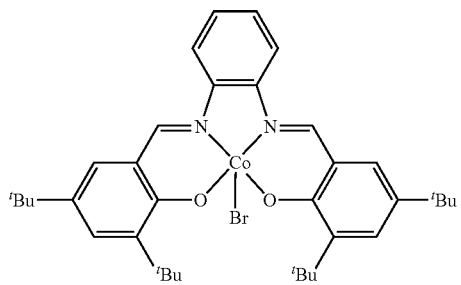
(X)

This compound is novel.

In yet another case, the compounds have the structure

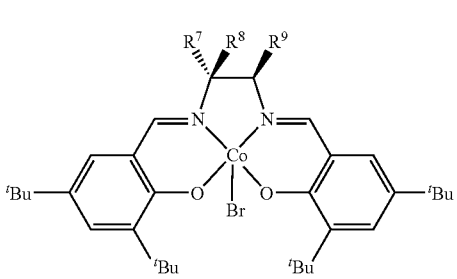
(XI)

where $R^7$ is Me, $R^8$ is H and $R^9$ is H; or where $R^7$ is Me, $R^8$ is Me and $R^9$ is H; or where $R^7$ is Ph, $R^8$ is H and $R^9$ is Ph.

The cobalt carboxylate compounds are made by adding oxygen and the appropriate carboxylic acid to the (salen)Co (II) complex. The cobalt halide compounds are made by reacting (salen)Co(III) tosylate complex with the appropriate sodium halide.

The term "salen" means any tetradentate ligand derived from a diamine and 2 equivalents of salicylaldehyde.

We turn now to the second embodiment.

Preferably the cocatalyst is a salt where the cation is

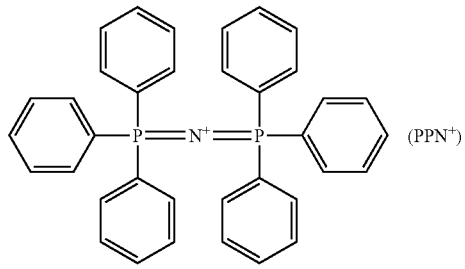
($PPN^+$)

and the anion is selected from the group consisting of $Cl^-$ and $OBzF_5^-$ where $OBzF_5$ is 2,3,4,5,6-pentafluorobenzoate. [PPN][$OBzF_5$] is novel.

Catalyst systems used in reactions set forth in working examples are: catalyst system where the catalyst has the structural Formula (VIII) where X is $OBzF_5$ and the cocatalyst is [PPN]Cl; catalyst system where the catalyst has the structural Formula (VIII) where X is Cl and the cocatalyst is [PPN][$OBzF_5$]; catalyst system where the catalyst has the structural formula (VIII) where X is Cl and the cocatalyst is [PPN]Cl; and catalyst system where the cocatalyst is $NBu_4Cl$ and the catalyst has the structural formula (VIII) where X is $OBzF_5$.

The [PPN]carboxylate complexes can be prepared by reacting [PPN]X with the appropriate sodium carboxylate.

We turn now to the third embodiment.

Preferably the $CO_2$ pressure ranges from 10 to 850 psi, the reaction temperature ranges from 20 to 25° C., the reaction time ranges from 0.5 to 4 hours, the catalyst has the structure (VIII) where X is Br, Cl or $OBzF_5$ and the alkylene oxide to catalyst ratio on a cobalt basis ranges from 400:1 to 600:1.

The alkylene oxide used herein can be, for example, rac-propylene oxide, or enantiomerically enriched-propylene oxide, e.g., S-propylene oxide or R-propylene oxide. Other epoxides such as butene oxide or cyclohexene oxide can also be employed.

We turn now to the fourth embodiment.

In a preferred case, the catalyst has the structural formula (VIII) where X is Cl and the cocatalyst is [PPN][$OBzF_5$].

In the experiments carried out, the propylene oxide was rac-propylene oxide.

We turn now to the fifth embodiment.

The polymers of the fifth embodiment can be made by the method of the fourth embodiment and working examples are set forth hereinafter.

We turn now to the sixth embodiment. The polymers of the sixth embodiment can be made by the methods of the third and fourth embodiments and working examples are set forth in Qin, Z., et al, Angew. Chem. Ind. Ed. 42, 5484-5487 (2003) and in working examples hereinafter.

The polymers of the fifth and sixth embodiments can be produced as crystalline polymers. Crystalline polymers have the advantage that they are mechanically strong and resist thermal deformation.

The poly(propylene carbonates) produced herein can be converted to polyurethanes by reaction with polyacid, polyol or water to make a poly(propylene carbonate) with two or more OR groups which in turn would be reacted with a diisocyanate to prepare polyurethane.

The invention is illustrated in Qin, Z., et al., Angew. Chem. Int. Ed. 42, 5484-5487 (2003) and in working examples below.

Working Example I

Synthesis of (VII) where R is Br, [(R,R)-(salen-8)CoOAc]

First (R,R)—N,N'-bis(5-bromo-3-tert-butyl-salicylidene)-1,2-cyclohexanediamine, [(R,R)-(salen-8)$H_2$], was synthesized as follows:

Under an atmosphere of nitrogen, to an aqueous solution of (R,R)-1,2-diaminocyclohexane L-tartrate (1.321 g, 5.0 mmol) and $K_2CO_3$ (1.382 g, 10.0 mmol) in water (10 mL) was added ethanol (50 mL). The mixture was heated to 80° C., and to it was dropwise added 5-bromo-3-tert-butyl-2-hydroxy-benzaldehyde, prepared by a modification of the methods described in Cavazzini, M., et al., Eur. J. Org. Chem. (2001), 4639-4649 and Lam, F., et al., J. Org. Chem. 61, 8414-8418 (1996) (2.571 g, 10.0 mmol) in THF (10 mL), resulting a yellow solution. After the mixture was stirred for 2 h and cooled down to room temperature, water (150 mL) was added to precipitate yellow crude title compound. The precipitate was redissolved in diethyl ether (100 mL) and washed with brine (100 mL), water (100 mL), and dried over anhydrous $Na_2SO_4$, and then concentrated. A yellow crystalline product was obtained after recrystallization from ethanol. Yield: 2.60 g, 88%. $^1$H NMR (CDCl$_3$, 500 MHz) δ 13.80 (s, 2H), 8.18 (s, 2H), 7.31 (d, $^4J$=2.0 Hz, 2H), 7.09 (d, $^4J$=2.0 Hz, 2H), 3.33 (br, 2H), 2.00 (br, 2H), 1.90 (br, 2H), 1.75 (M, 2H), 1.47 (m, 2H), 1.38 (s, 18H), $^{13}$C NMR (CDCl$_3$, 125 MHz) δ 24.40, 39.31, 159.57, 164.68, LRMS (EI) Cald. 592. found 592.

(R,R)—N,N'-bis(5-bromo-3-tert-butylsalicylidene)-1,2-diaminocyclohexane cobalt (II), [(R,R)-(salen-8)Co], was prepared as follows:

To a solution of the ligand [(R,R)-(salen-8)H$_2$] (1.777 g, 3.0 mmol) in toluene (10 mL) under nitrogen was added a solution of Co(OAc)$_2$ (0.708 g, 4 mmol) in MeOH (10 mL) via a cannula, affording a dark red precipitate. The mixture was stirred at 80° C. for 2 h. After the reaction mixture was cooled down to room temperature and concentrated in vacuo, the residue was dissolved in CH$_2$Cl$_2$ (50 mL) and passed through a celite pad to remove the excess Co(OAc)$_2$. Removing solvent of the filtrate afforded a dark red powder. Yield: 1.85 g, 95%. The molecular structure of this complex was determined by single crystal X-ray diffraction.

(R,R)—N,N'-bis(5-bromo-3-tert-butylsalicylidene)-1,2-diaminocyclohexane cobalt (III) acetate, [(R,R)-(salen-8)CoOAc] was prepared as follows:

To a solution of the [(R,R)-(salen-8)Co] (1.750 g, 2.70 mmol) in toluene (15 mL) and CH$_2$Cl$_2$ (50 mL) was added acetic acid (1.62 g, 27.0 mmol). The solution quickly changed from red to brown. After 2 h, all solvents and excess acetic acid were removed and the residue was dried to constant weight under vacuum, quantitatively affording a brown powder. $^1$H NMR (CD$_2$Cl$_2$, 400 MHz) δ 7.52 (s, 1H), 7.43 (br, 2H), 7.34 (d, $^4J$=2.4 Hz, 1H), 7.32 (d, $^4J$=2.4 Hz, 1H), 7.14 (s, 1H), 4.16 (m, 1H), 3.22 (M, 1H), 2.81 (M. 1H), 2.74 (M, 1H), 2.00 (M, 2H), 1.96 (br, 1H), 1.89 (br, 2H), 1.73 (M, 1H), 1.53 (s, 3H), 1.48 (s, 9H), 1.24 (s, 9H).

Working Example II

Synthesis of (VII) where R is H, [(R,R)-(salen-7)CoOAc]

(R,R)—N,N'—Bis(3-tert-butyl-salicylidene)-1,2-cyclohexanediamine, [(R,R)-(salen-7)H$_2$] was prepared as described in Pospisil, P. J., et al., Chem. Eur. J. 2, 974-980 (1996).

(R,R)—N,N'-bis(3-tert-butylsalicylidene)-1,2-diaminocyclohexane cobalt, [(R,R)-(salen-7)Co] was prepared from [(R,R)-(salen-7)H$_2$] by a similar procedure to that used for [(salen-8)Co] in working Example I. The yield was 98%.

(R,R)—N,N'-bis(3-tert-butylsalicylidene)-1,2-diaminocyclohexane cobalt (III) acetate, [(R,R)-(salen-7)CoOAc] was prepared in similar fashion to [(R,R)-(salen-8)CoOAc] except only toluene was used as solvent. A dark brown powder was obtained quantitatively. $^1$H NMR (CD$_2$Cl$_2$, 400 MHz) δ 7.60 (s, 1H), 7.42 (s, 1H), 7.28 (s, 2H), 7.20 (s, 2H), 6.62 (s, 1H), 6.43 (s, 1H), 4.39 (s, 1H), 3.38 (s, 1H), 2.84 (br, 2H), 1.77-2.20 (br M, 6H), 1.56 (br, 12H), 1.38 (s, 9H).

Working Example III

Synthesis of (VII) where R is $^t$Bu and (VIII) where X is OAc, [(R,R)-(salen-1)CoOAc]

(R,R)—N,N'-bis(3,5-di-tert-butylsalicylidene)-1,2-diaminocyclohexane cobalt (In) acetate, [(R,R)-(salen-1)CoOAc] is synthesized as described in Schaus, S. E., et al., J. Am. Chem. 124, 1307-1315 (2002) and Tokunaga, M., Science 277, 936-938 (1997). The material here was purchased from Strem.

Working Example IV

Copolymerizations

Copolymerizations of propylene oxide (PO) and CO$_2$ were carried out as follows using [(R,R)-(salen-8)CoOAc], the product of Working Example I, [(R,R)-(salen-7)CoOAc], the product of Working Example II, [(R,R)-(salen-1)CoOAc], the product of Working Example III, [Zn(BDI)OAc] prepared as described in Allen, S. D., et al., J. Am. Chem. Soc. 124, 14284-14285 (2002), Reference [14], and [Cr(salph)Cl] prepared as described in Darensbourg, D. J., et al., J. Am. Chem. Soc. 125, 7586-7591 (2003), Reference [16]:

General PO/CO$_2$ copolymerization Procedure: A glass tube equipped with a stir bar was charged with catalyst, and then was inserted into a pre-dried 100 mL Parr autoclave. After the assembled autoclave was evacuated under vacuum and refilled with nitrogen for three times, PO was added through a valve using a syringe. The autoclave was brought to appropriate temperature, and then pressurized to the appropriate pressure with CO$_2$. After the allotted reaction time, the unreacted PO was recovered using vacuum transfer and analyzed by a chiral GC. A small amount of the residue was removed for $^1$H NMR analysis. The crude polymer was dissolved in CH$_2$Cl$_2$ (10-20 mL), and then a small amount of MeOH was added. The polymer was precipitated from diethyl ether, collected by filtration and dried in vacuo to constant weight.

Conditions and results are set forth in Table 1 below.

TABLE 1

| Entry[a] | Catalyst | Epoxide | [PO]:[Cat] | Pressure (psi) | Temp (° C.) | Time (h) | TOF[b] (h$^{-1}$) | Selectivity (% PPC)[c] | Carbonate Linkages (%)[c] | $M_n$[d] (g/mol) | PDI ($M_w/M_n$) |
|---|---|---|---|---|---|---|---|---|---|---|---|
| 1 | [(R,R)-(salen-8)CoOAc] | rac-PO | 500 | 800 | 25 | 3 | 81 | >99 | 95 | 15 300 | 1.22 |
| 2 | [(R,R)-(salen-8)CoOAc] | rac-PO | 500 | 600 | 25 | 3 | 19 | >99 | 94 | 3100 | 2.60 |
| 3 | [(R,R)-(salen-8)CoOAc] | rac-PO | 500 | 800 | 40 | 3 | 17 | >99 | 90 | 5600 | 1.21 |
| 4 | [(R,R)-(salen-8)CoOAc] | rac-PO | 500 | 800 | 30 | 3 | 69 | >99 | 94 | 12 200 | 1.26 |
| 5 | [(R,R)-(salen-8)CoOAc] | rac-PO | 500 | 800 | 20 | 3 | 42 | >99 | 95 | 8000 | 1.44 |
| 6 | [(R,R)-(salen-8)CoOAc] | rac-PO | 500 | 800 | 15 | 3 | 31 | >99 | 95 | 7600 | 1.51 |
| 7 | [(R,R)-(salen-8)CoOAc] | rac-PO | 200 | 800 | 25 | 3 | 51 | >99 | 95 | 8200 | 1.25 |

TABLE 1-continued

| Entry[a] | Catalyst | Epoxide | [PO]:[Cat] | Pressure (psi) | Temp (° C.) | Time (h) | TOF[b] ($h^{-1}$) | Selectivity (% PPC)[c] | Carbonate Linkages (%)[c] | $M_n$[d] (g/mol) | PDI ($M_w/M_n$) |
|---|---|---|---|---|---|---|---|---|---|---|---|
| 8 | [(R,R)-(salen-8)CoOAc] | rac-PO | 2000 | 800 | 25 | 8 | 38 | >99 | 95 | 21 700 | 1.41 |
| 9 | [(R,R)-(salen-7)CoOAc] | rac-PO | 200 | 800 | 25 | 3 | 51 | >99 | 96 | 6600 | 1.21 |
| 10 | [(R,R)-(salen-7)CoOAc] | rac-PO | 500 | 800 | 25 | 3 | 66 | >99 | 96 | 9000 | 1.31 |
| 11 | [(R,R)-(salen-1)CoOAc] | rac-PO | 200 | 800 | 25 | 3 | 42 | >99 | 99 | 5700 | 1.28 |
| 12 | [(R,R)-(salen-1)CoOAc] | rac-PO | 500 | 800 | 25 | 3 | 59 | >99 | 99 | 8100 | 1.57 |
| 13 | [(R,R)-(salen-1)CoOAc] | (S)-PO | 500 | 800 | 25 | 3 | 71 | >99 | 99 | 6900 | 1.58 |
| 14[e] | [Zn(BDI)OAc] | rac-PO | 2000 | 300 | 25 | 2 | 184 | 87 | 99 | 35 900 | 1.11 |
| 15[f] | [Cr(salph)Cl] | rac-PO | 1500 | 490 | 75 | 4 | 160 | 71 | 98 | 16 700 | 1.38 |

All of the polymerizations were carried out in 3.5 mL of neat propylene oxide (PO).
[b]Turnover frequency of PO to PPC.
[c]Determined by using $^1$H NMR spectroscopy.
[d]Determined by gel permeation chromatography in tetrahydrofuran at 40° C., calibrated with polystyrene standards.
[e]Reference [14].
[f]Reference [16].

As indicated by the percent selectivity (% PPC) for entries 1-13 of Table 1, cyclic propylene carbonate was not formed. [(R,R)-(salen-1)CoOAc] was found to be highly regioselective with 80% head to tail linkages. In contrast, the catalysts [(R,R)-(salen-8)CoOAc], [(R,R)-(salen-7)CoOAc] and [Zn(BDI) OAc] gave typical regioselectivities of 70, 75 and 60%, respectively.

Polymerization of (S)-propylene oxide with enantiomerically pure [(R,R)-(salen-1)CoOAc], entry 13 in Table 1, yielded isotactic (S) polymer with head-to-tail content of 93%.

Working Example V

Synthesis of (VIII) where X is I[[(R,R)-(salen-1)CoI]

(R,R)—N,N'-bis(3,5-di-tert-butylsalicylidene)-1,2-diaminocyclohexane cobalt [(R,R)-(salen-1)Co] was purchased from Aldrich and recrystallized from methylene chloride and methanol.

(R,R)—N,N'-bis(3,5-di-tert-butylsalicylidene)-1,2-diaminocyclohexane cobalt (III) iodide, [(R,R)-(salen-1)CoI] is synthesized as described in Nielsen, L. P. C.; Stevenson, C. P.; Blackmond, D. G.; Jacobsen, E. N. *J. Am. Chem. Soc.* 2004, 126, 1360-1362 with the substitution of NaI for NaCl. $^1$H NMR (DMSO-$d_6$, 500 MHz): δ1.32 (s, 18H) 1.63 (m, 2H), 1.76 (s, 18H), 1.91 (m, 2H), 2.02 (m, 2H), 3.10 (m, 2H), 3.66 (m, 2H), 7.45 (d, $^4$J=2.5 Hz, 2H), 7.50 (d, $^4$J=2.5 Hz, 2H), 7.83 (s, 2H). $^{13}$C NMR (DMSO-$d_6$, 125 MHz): δ24.23, 29.54, 30.36, 31.49, 33.47, 35.71, 69.22, 118.59, 128.63, 129.16, 135.82, 141.74, 161.95, 164.49. Anal. Calcd for $C_{36}H_{52}N_2O_2CoI$: C, 59.18; H, 7.17; N, 3.83. Found: C, 59.14; H, 7.05; N, 3.75.

Working Example VI

Synthesis of (VIII) where X is Br [(R,R)-(salen-1)CoBr]

(R,R)—N,N'-bis(3,5-di-tert-butylsalicylidene)-1,2-diaminocyclohexane cobalt [(R,R)-(salen-1)Co] was purchased from Aldrich and recrystallized from methylene chloride and methanol.

(R,R)—N,N'-bis(3,5-di-tert-butylsalicylidene)-1,2-diaminocyclohexane cobalt (III) bromide, [(R,R)-(salen-1)CoBr] is synthesized as described in Nielsen, L. P. C.; Stevenson, C. P.; Blackmond, D. G.; Jacobsen, E. N. *J. Am. Chem. Soc.* 2004, 126, 1360-1362 with the substitution of NaBr for NaCl. $^1$H NMR (DMSO-$d_6$, 500 MHz): δ1.30 (s, 18H), 1.58 (m, 2H), 1.74 (s, 18H), 1.92 (m, 2H), 2.00 (m, 2H), 3.06 (m, 2H), 3.59 (m, 2H), 7.44 (d, $^4$J=3.0 Hz, 2H), 7.47 (d, $^4$J=3.0 Hz, 2H), 7.83 (s, 2H). $^{13}$C NMR (DMSO-$d_6$, 125 MHz): δ24.32, 29.57, 30.43, 31.55, 33.58, 35.82, 69.32, 118.61, 128.78, 129.28, 135.87, 141.84, 162.11, 164.66. Anal. Calcd for $C_{36}H_{52}N_2O_2CoBr$: C, 63.25; H, 7.67; N, 4.10. Found: C, 63.05; H, 7.69; N, 4.06.

Working Example VII

Synthesis of (VIII) where X is Cl[(R,R)-(salen-1)CoCl]

(R,R)—N,N'-bis(3,5-di-tert-butylsalicylidene)-1,2-diaminocyclohexane cobalt (III) chloride, [(R,R)-(salen-1)CoCl] was prepared as previously described in Nielsen, L. P. C.; Stevenson, C. P.; Blackmond, D. G.; Jacobsen, E. N. *J. Am. Chem. Soc.* 2004, 126, 1360-1362. Additional characterization: $^{13}$C NMR (DMSO-d$_6$, 125 MHz): δ24.34, 29.51, 30.40, 31.56, 33.51, 35.78, 69.27, 118.58, 128.78, 129.28, 135.86, 141.84, 162.08, 164.68.

Working Example VIII

Synthesis of (VIII) where X is OBzF$_5$-[(R,R)-(salen-1)CoOBzF$_5$]

(R,R)—N,N'-bis(3,5-di-tert-butylsalicylidene)-1,2-diaminocyclohexane cobalt [(R,R)-(salen-1)Co] was purchased from Aldrich and recrystallized from methylene chloride and methanol.

[(R,R)-(salen-1)Co] (1.2 g, 2.0 mmol) and pentafluorobenzoic acid (0.42 g, 2.0 mmol) were added to a 50 mL round-bottomed flask charged with a Teflon stir bar. Toluene (20 mL) was added to the reaction mixture, and it was stirred open to air at 22° C. for 12 h. The solvent was removed by rotary evaporation at 22° C., and the solid was suspended in 200 mL of pentane and filtered. The dark green crude material was dried in vacuo and collected in quantitative yield. $^1$H NMR (DMSO-d$_6$, 500 MHz): δ1.30 (s, 18H), 1.59 (m, 2H), 1.74 (s, 18H), 1.90 (m, 2H), 2.00 (m, 2H), 3.07 (m, 2H), 3.60 (m, 2H), 7.44 (d, $^4$J=2.5 Hz, 2H), 7.47 (d, $^4$J=3.0 Hz, 2H), 7.81 (s, 2H). $^{13}$C NMR (DMSO-d$_6$, 125 MHz): δ24.39, 29.61, 30.13, 30.42, 31.55, 33.57, 35.83, 69.38, 118.59, 128.78, 129.29, 135.86, 141.83, 162.21, 164.66. Carbons on the phenyl group of pentafluorobenzoate were not assigned in the $^{13}$C NMR spectrum owing to complex carbon fluorine splitting patterns. $^9$F NMR (470 MHz, DMSO-d$_6$): δ−163.32 (m), −162.50 (m), −144.48 (m). Anal. Calcd for C$_{43}$H$_{52}$O$_4$N$_2$F$_5$Co—H$_2$O: C, 62.01; H, 6.54; N, 3.36. Found: C, 62.25; H, 6.38; N, 3.42.

Working Example IX

Synthesis of (IX) where R$^{11}$ is $^t$Bu and R$^{10}$ is H [(R,R)-(salen-7)CoBr]

(R,R)—N,N'-bis(3-tert-butylsalicylidene)-1,2-diaminocyclohexane cobalt [(R,R)-(salen-7)Co] is synthesized as described in Sun, W.; Xia, C.-G.; Zhao, P.-Q. J Mol Catal A: Chem 2002, 184, 51.

(R,R)—N,N'-bis(3-tert-butylsalicylidene)-1,2-diaminocyclohexane cobalt (III) bromide [(R,R)-(salen-7)CoBr] was prepared as follows: [(R,R)-(Salen-7)Co] (470 mg, 0.96 mmol) and p-toluenesulfonic acid monohydrate (190 mg, 1.0 mmol) were added to a 50 mL round-bottomed flask with a Teflon stir bar, and 10 mL of methylene chloride was added. The mixture was stirred open to air for 1 h at 22° C., and the methylene chloride was removed in vacuo. The solid was suspended in pentane and filtered to afford the intermediate [(R,R)-(salen-7)CoOTs] (OTs=tosylate). This solid was dissolved in 25 mL of methylene chloride and added to a 100 mL separatory funnel. The organic layer was rinsed with saturated aqueous NaBr (3×25 mL). The organic layer was dried over Na$_2$SO$_4$, filtered and dried in vacuo. The crude material was suspended in pentane and filtered to afford the solid [(R,R)-(salen-7)CoBr] (210 mg, 38%). $^1$H NMR (DMSO-d$_6$, 500 MHz): δ 1.59 (m, 2H), 1.73 (s, 18H), 1.90 (m, 2H), 2.01 (m, 2H), 3.06 (m, 2H), 3.60 (m, 2H), 6.59 (t, $^3$J=7.0 Hz, 2H), 7.38 (d, $^3$J=7.0 Hz, 2H), 7.49 (d, $^3$J=7.0 Hz, 2H), 7.87 (s, 2H). $^{13}$C NMR (DMSO-d$_6$, 125 MHz): δ 24.18, 29.49, 30.31, 35.62, 69.33, 114.47, 119.19, 131.17, 133.83, 142.49, 164.19, 164.37.

Working Example X

Synthesis of (IX) where R$^{11}$ is $^t$Bu and R$^{10}$ is Br [(R,R)-(salen-8)CoBr]

The procedure for the synthesis of [(R,R)-(salen-7)CoBr] was applied to the synthesis of (R,R)—N,N'-bis(5-bromo-3-tert-butylsalicylidene)-1,2-diaminocyclohexane cobalt (III) bromide (R,R)-(salen-8)CoBr; however, [(R,R)-(salen-8)Co] (synthesis described above) (360 mg, 0.56 mmol) and p-toluenesulfonic acid monohydrate (110 mg, 0.60 mmol) were stirred for 12 h in methylene chloride (10 mL). Following the salt metathesis with NaBr, the product (R,R)-(salen-8)CoBr was obtained (180 mg, 44%). $^1$H NMR (DMSO-d$_6$, 500 MHz): δ 1.59 (m, 2H), 1.71 (s, 18H), 1.88 (m, 2H), 2.00 (m, 2H), 3.04 (m, 2H), 3.61 (m, 2H), 7.37 (d, $^4$J=2.5 Hz, 2H), 7.80 (d, $^4$J=2.5 Hz, 2H), 7.96 (s, 2H). $^{13}$C NMR (DMSO-d$_6$, 125 MHz): δ 24.06, 29.51, 29.85, 35.78, 69.55, 104.97, 120.73, 133.45, 135.04, 145.16, 163.19, 164.22.

Working Example XI

Synthesis of (IX) where R$^{11}$ is Me and R$^{10}$ is H [(R,R)-(salen-10)CoBr]

(R,R)—N,N'—Bis(3-methylsalicylidene)-1,2-diaminocyclohexane cobalt [(R,R)-(salen-10)Co] is synthesized as described in Szlyk, E.; Surdykowski, A.; Barwiolek, M.; Larsen, E. Polyhedron 2002, 21, 2711.

The procedure for the synthesis of [(R,R)-(salen-7)CoBr] was applied to the synthesis of (R,R)—N,N'-bis(3-methylsalicylidene)-1,2-diaminocyclohexane cobalt (III) bromide [(R,R)-(salen-10)CoBr], however; [(R,R)-(salen-10)Co] (210 mg, 0.52 mmol) and p-toluenesulfonic acid monohydrate (100 mg, 0.53 mmol) were stirred for 2 h in methylene chloride (20 mL). An excess of methylene chloride (200 mL) was used in the salt metathesis with NaBr in order to dissolve all of the [(R,R)-(salen-10)CoOTs] intermediate. Following this reaction, the product [(R,R)-(salen-10)CoBr] was obtained (170 mg, 67%). $^1$H NMR (DMSO-d$_6$, 500 MHz): δ 1.57 (m, 2H), 1.86 (m, 2H), 1.99 (m, 2H), 2.64 (s, 6H), 3.05 (m, 2H), 3.63 (m, 2H), 6.58 (t, $^3$J=7.0 Hz, 2H), 7.31 (d, $^3$J=7.0 Hz, 2H), 7.48 (d, $^3$J=7.0 Hz, 2H), 8.02 (s, 2H). $^{13}$C NMR (DMSO-d$_6$, 125 MHz): δ 17.12, 24.17, 29.45, 69.60, 114.57, 117.89, 130.68, 132.86, 134.36, 163.32, 164.13.

Working Example XII

Synthesis of (DC) where R$^{11}$ is CPh (CH$_3$), and R$^{10}$ is CPh (CH$_3$)$_2$ [(R,R)-(salen-11)CoBr]

3,5-Bis(α,α'-dimethylbenzyl)-2-hydroxybenzaldehyde was synthesized as described in A. E. Cheman, E. B. Lobkovsky and G. W. Coates, *Macromolecules*, 2005, 38, 6259-6268.

Synthesis of (R,R)—N,N'-bis(3,5-bis(α,α'-dimethylbenzyl)salicylidene)-1,2-diaminocyclohexane, [(R,R)-(salen-11)H$_2$]: (R,R)-1,2-Diaminocyclohexane-L-tartrate (0.74 g, 2.8 mmol) and K$_2$CO$_3$ (0.77 g, 5.6 mmol) were stirred in H$_2$O (8 mL) until all was dissolved. To it was added a solution of 3,5-bis(α,α'-dimethylbenzyl)-2-hydroxybenzaldehyde (2.0 g, 5.6 mmol) in ethyl alcohol (35 mL) and the mixture was refluxed for 3 h. The reaction mixture was then cooled to 22°

C., filtered, and washed thoroughly with $H_2O$ and then with cold ethyl alcohol. The crude yellow solid was dried and collected (1.8 g, 81%). $^1$H NMR (CDCl$_3$, 500 MHz): δ 1.29 (m, 2H), 1.52 (m, 2H), 1.59 (s, 6H), 1.67 (s, 12H), 1.68 (s, 6H), 1.73 (m, 4H), 3.11 (m, 2H), 6.94 (d, $^4$J=2.5 Hz, 2H), 7.16 (tt, $^3$J=7.0 Hz, $^4$J=1.5 Hz, 2H), 7.16-7.29 (m, 20H), 8.08 (s, 2H), 13.21 (broad s, 2H). $^{13}$C NMR (CDCl$_3$, 125 MHz): δ 24.31, 28.71, 30.38, 30.95, 31.04, 33.22, 42.25, 42.44, 72.25, 118.01, 125.11, 125.68, 125.70, 126.78, 127.74, 127.92, 128.11, 129.27, 135.82, 139.46, 150.64, 150.76, 157.77, 165.38. HRMS (ESI) m/z calcd ($C_{56}H_{62}N_2O_2+H^+$) 795.4890. found 795.4900.

Synthesis of (R,R)—N,N'-bis(3,5-bis(α,α'-dimethylbenzyl)salicylidene)-1,2-diaminocyclohexane cobalt, [(R,R)-(salen-11)Co]: [(R,R)-(salen-11)H$_2$] (0.69 g, 0.87 mmol) and cobalt acetate tetrahydrate (0.26 g, 1.0 mmol) were added to a Schlenk flask charged with a Teflon stir bar under N$_2$. A 1:1 mixture of toluene and methanol (30 mL); (degassed for 20 min by sparging with dry N$_2$) was added and stirred at 22° C. for 2 h. The resultant red precipitate was filtered in air and washed with distilled water (50 mL) and methanol (50 mL) and collected as a crude solid (0.59 g, 80%). IR (KBr, cm$^{-1}$): 766, 809, 1034, 1105, 1246, 1325, 1340, 1362, 1459, 1528, 1605, 2872, 2937, 2968, 3026, 3061, 3453. HRMS (ESI) m/z calcd ($C_{56}H_{60}CoN_2O_2$) 851.3987. found 851.3972.

Synthesis of (R,R)—N,N'-bis(3,5-bis(α,α'-dimethylbenzyl)salicylidene)-1,2-diaminocyclohexane cobalt (III) bromide, [(R,R)-(salen-11)CoBr]: [(R,R)-(salen-11)Co] (0.50 g, 0.59 mmol) and p-toluenesulfonic acid monohydrate (0.11 g, 0.59 mmol) were added to a 50 mL round bottomed flask charged with a Teflon stir bar. Methylene chloride (10 mL) was added to the reaction mixture and stirred for 2 h open to air at 22° C. The solvent was removed by rotary evaporation at 22° C., and the crude solid was washed with pentane (100 mL) and filtered. The crude material was dissolved in methylene chloride (25 mL) and added to a 125 mL separatory funnel. The organic layer was rinsed with saturated aqueous NaBr (3×25 mL). The organic layer was dried over Na$_2$SO$_4$ and evaporated under reduced pressure. The solid was washed with pentane (100 mL) and filtered to afford [(R,R)-(salen-11)CoBr] (0.16 g, 29%).

Working Example XIII

Synthesis of (X)-[(salen-6)CoBr]

N,N'-bis(3,5-di-tert-butylsalicylidene)-1,2-diaminophenylene cobalt, [(salen-6)Co] is synthesized as described in H. Shimakoshi, H. Takemoto, I. Aritome and Y. Hisaeda, *Tetrahedron Lett.*, 2002, 43, 4809-4812.

Employing the same reaction conditions as for [(R,R)-(salen-11)CoBr], [(salen-6)Co] (1.0 g, 1.7 mmol) and p-toluenesulfonic acid monohydrate (0.32 g, 1.7 mmol) were used to produce N,N'-bis(3,5-di-tert-butylsalicylidene)-1,2-diaminophenylene cobalt (III) bromide, [(salen-6)CoBr] (0.35 g, 30%). $^1$H NMR (DMSO-d$_6$, 500 MHz): δ 1.35 (s, 18H), 1.78 (s, 18H), 7.55 (d, $^4$J=2.5 Hz, 2H), 7.56 (td, $^3$J=6.5 Hz, $^4$J=3.5 Hz, 2H), 7.66 (d, $^4$J=2.5 Hz, 2H), 8.63 (dd, $^3$J=6.5 Hz, $^4$J=3.5 Hz, 2H), 8.95 (s, 2H). $^{13}$C NMR (DMSO-d$_6$, 125 MHz): δ 30.34, 31.34, 33.79, 36.01, 117.40, 117.45, 128.14, 129.97, 131.00, 136.59, 142.07, 144.72, 161.60, 165.59. HRMS (ED m/z calcd ($C_{36}H_{46}BrCoN_2O_2$—Br) 597.2891. found 597.2878.

Working Example XIV

Synthesis of (XI) where $R^7$ is Me, $R^8$ is H and $R^9$ is H [(R)-(salen-2)CoBr]

(R)—N,N'-bis(3,5-di-tert-butylsalicylidene)-1,2-diaminopropane [(R)-(salen-2)H$_2$] was synthesized as described in D. J. Darensbourg, R. M. Mackiewicz, J. L. Rodgers, C. C. Fang, D. R. Billodeaux and J. H. Reibenspies, *Inorg. Chem.*, 2004, 43, 6024-6034.

(R)—N,N'-bis(3,5-di-tert-butylsalicylidene)-1,2-diaminopropane cobalt [(R)-(salen-2)Co] was synthesized as follows: Employing the same reaction conditions as for [(R,R)-(salen-11)Co], [(R)-(salen-2)H$_2$] (2.8 g, 5.5 mmol) and cobalt acetate tetrahydrate (1.7 g, 6.8 mmol) in a 1:1 mixture of degassed toluene and methanol (150 mL) were used to afford a crude red solid (2.9 g, 95%). IR (KBr, cm$^{-1}$): 787, 837, 874, 1179, 1204, 1255, 1320, 1361, 1385, 1466, 1528, 1596, 2871, 2909, 2956. HRMS (ES) m/z calcd ($C_{33}H_{48}CoN_2O_2$) 563.3048. found 563.3046.

(R)—N,N'-bis(3,5-di-tert-butylsalicylidene)-1,2-diaminopropane cobalt (III) bromide [(R)-(salen-2)CoBr] was synthesized as follows: [(R)-(salen-2)Co] (1.0 g, 1.8 mmol) and p-toluenesulfonic acid monohydrate (0.34 g, 1.8 mmol) were added to a 50 mL round-bottomed flask charged with a Teflon stir bar. Methylene chloride (30 mL) was added to the reaction mixture and stirred for 2 h open to air at 22° C. The solvent was removed by rotary evaporation at 22° C., and the crude dark green solid was dissolved in pentane (50 mL) and filtered. The solvent was removed by rotary evaporation, and the material was dissolved in methylene chloride (50 mL) and added to a 250 mL separatory funnel. The organic layer was shaken vigorously with saturated aqueous NaBr (3×50 mL). The organic layer was dried over Na$_2$SO$_4$ and evaporated under reduced pressure. The solid was suspended in pentane and filtered to afford a crude black solid (0.50 g, 43%). $^1$H NMR (DMSO-d$_6$, 500 MHz): δ 1.30 (s, 18H), 1.61 (d, $^3$J=6.5 Hz, 3H), 1.73 (s, 18H), 3.86 (m, 1H), 4.21 (m, 1H), 4.32 (m, 1H), 7.33 (d, $^4$J=2.0 Hz, 1H), 7.40 (d, $^4$J=2.0 Hz, 1H), 7.44 (s, 1H), 7.45 (s, 1H), 7.93 (s, 1H), 8.09 (s, 1H). $^{13}$C NMR (DMSO-d$_6$, 125 MHz): δ 18.45, 30.34, 30.38, 31.51, 31.54, 33.39, 33.43, 35.71, 35.73, 62.99, 64.57, 118.57, 118.88, 128.15, 128.67, 128.74, 128.82, 135.84, 136.01, 141.73, 142.01, 161.67, 161.94, 167.03, 168.55. HRMS (ED) m/z calcd. ($C_{33}H_{48}BrCoN_2O_2$—Br) 563.3048. found 563.3037.

Working Example XV

Synthesis of (XI) where $R^7$, $R^8$ and $R^9$ are H [(salen-3)CoBr]

N,N'-bis(3,5-di-tert-butylsalicylidene)-1,2-diaminoethane cobalt [(salen-3)Co] was synthesized as described in B. Rhodes, S. Rowling, P. Tidswell, S. Woodward and S. M. Brown, *J Mol Catal A: Chem*, 1997, 116, 375-384.

Synthesis of N,N'-bis(3,5-di-tert-butylsalicylidene)-1,2-diaminoethane cobalt (III) bromide [(salen-3)CoBr]: Employing the same reaction conditions as for [(R,R)-(salen-2)CoBr], [(salen-3)Co] (0.30 g, 0.55 mmol) and p-toluenesulfonic acid monohydrate (0.10 g, 0.55 mmol) were used. Following the salt metathesis with NaBr, the crude product [(salen-5)CoBr] was obtained (86 mg, 25%). $^1$H NMR (DMSO-d$_6$, 500 MHz): δ 1.30 (s, 18H), 1.73 (s, 18H), 4.14 (s, 4H), 7.31 (d, $^4J$=3.0 Hz, 2H), 7.45 (d, $^4J$=3.0 Hz, 2H), 8.12 (s, 2H). $^{13}$C NMR (DMSO-d$_6$, 125 MHz): δ 30.36, 31.52, 33.43, 35.77, 58.24, 118.51, 128.27, 128.74, 135.93, 142.05, 162.13, 168.65. HRMS (EI) m/z calcd (C$_{32}$H$_{46}$BrCoN$_2$O$_2$—Br) 549.2891. found 549.2885.

Working Example XVI

Synthesis of (XI) where R$^7$ is Me, R$^8$ is Me and R$^9$ is H [(salen-4)CoBr]

Synthesis of N,N'-bis(3,5-di-tert-butylsalicylidene)-2-methyl-1,2-diaminopropane [(salen-4)H$_2$]: To a solution of 3,5-di-tert-butyl-2-hydroxybenzaldehyde (3.0 g, 13 mmol) in ethyl alcohol (60 mL) was added 2-methyl-1,2-propanediamine (0.67 mL, 6.4 mmol) and the mixture was refluxed for 3 h. The reaction was cooled to 22° C., and the solvent was removed in vacuo. The crude yellow solid was recrystallized from ethyl alcohol at −20° C. affording yellow needles (3.1 g, 93%). $^1$H NMR (CDCl$_3$, 500 MHz): δ 1.28 (s, 9H), 1.29 (s, 9H), 1.43 (s, 24H), 3.71 (s, 2H), 7.07 (d, $^4J$=4.5 Hz, 1H), 7.09 (d, $^4J$=4.5 Hz, 1H), 7.35 (d, $^4J$=4.5 Hz, 1H), 7.36 (d, $^4J$=4.5 Hz, 1H), 8.35 (s, 1H), 8.39 (s, 1H) 13.67 (s, 1H), 14.21 (s, 1H). $^{13}$C NMR (CDCl$_3$, 125 MHz): δ 25.73, 29.60, 29.63, 31.63, 31.66, 34.26, 35.17, 35.19, 60.14, 70.71, 117.99, 118.08, 126.22, 126.35, 126.90, 127.18, 136.78, 136.80, 139.98, 140.12, 158.32, 158.52, 162.88, 167.78. HRMS (ESI) m/z/z calcd (C$_{34}$H$_{52}$N$_2$O$_2$+H$^+$) 521.4107. found 521.4110.

Synthesis of N,N'-bis(3,5-di-tert-butylsalicylidene)-2-methyl-1,2-diaminopropane cobalt [(Salen-4)Co]: [(Salen-4)H$_2$] (2.3 g, 4.4 mmol) and cobalt acetate tetrahydrate (1.3 g, 5.2 mmol) were added to a Schlenk flask charged with a Teflon stir bar under N$_2$. A 1:1 mixture of toluene and methanol (100 mL); (degassed for 20 min by sparging with dry N$_2$) was added and stirred at 22° C. for 2 h. The resultant red precipitate was filtered in air and washed with distilled water (50 mL) and methanol (50 mL) and collected as a crude solid (2.3 g, 90% yield). IR (KBr, cm$^{-1}$): 786, 842, 871, 1178, 1255, 1318, 1363, 1390, 1464, 1528, 1595, 2870, 2909, 2959. HRMS (ESI) m/z calcd (C$_{34}$H$_{50}$CoN$_2$O$_2$) 577.3204. found 577.3226.

Synthesis of N,N'-bis(3,5-di-tert-butylsalicylidene)-2-methyl-1,2-diaminopropane cobalt (III) bromide [(salen-4)CoBr]: [(salen-4)Co] (0.30 g, 0.52 mmol) and p-toluenesulfonic acid monohydrate (99 mg, 0.52 mmol) were added to a 50 mL round-bottomed flask charged with a Teflon stir bar. Methylene chloride (30 mL) was added to the reaction mixture and stirred for 2 h open to air at 22° C. The solvent was removed by rotary evaporation at 22° C., and the crude dark green solid was dissolved in pentane (50 mL) and filtered. The solvent was removed by rotary evaporation, and the material was dissolved in methylene chloride (50 mL) and added to a 250 mL separatory funnel. The organic layer was shaken vigorously with saturated aqueous NaBr (3×50 mL). The organic layer was dried over Na$_2$SO$_4$ and evaporated under reduced pressure. The solid was suspended in pentane and filtered to afford a crude black solid (92 mg, 27%). $^1$H NMR (DMSO-d$_6$, 500 MHz): δ 1.30 (s, 9H), 1.32 (s, 9H), 1.63 (s, 6H), 1.73 (s, 9H), 1.74 (s, 9H), 4.02 (s, 2H), 7.36 (d, $^4J$=2.5 Hz, 1H), 7.45 (d, $^4J$=2.5 Hz, 1H), 7.475 (s, 1H), 7.482 (s, 1H), 7.88 (s, 1H), 8.03 (s, 1H). $^{13}$C NMR (DMSO-d$_6$, 125 MHz): δ 27.10, 30.35, 31.28, 31.32, 31.55, 31.61, 33.43, 33.50, 35.72, 35.77, 66.98, 70.93, 118.36, 119.57, 128.05, 128.75, 128.98, 129.35, 135.85, 136.41, 141.42, 142.12, 161.11, 161.96, 166.31, 168.37. HRMS (ED m/z calcd (C$_{34}$H$_{50}$BrCoN$_2$O$_2$—Br) 577.3204. found 577.3199.

Working Example XVII

Synthesis of (XI) where R$^7$ is Ph, R$^8$ is H and R$^9$ is Ph, [(R,R)-(salen-5)CoBr]

The synthesis of (R,R)—N,N'-bis(3,5-di-tert-butylsalicylidene)-1,2-diphenylethylenediamino cobalt (II) [(R,R)-(salen-5)Co] is described in T. Fukuda and T. Katsuki, *Tetrahedron*, 1997, 53, 7201-7208.

Synthesis of (R,R)—N,N'-bis(3,5-di-tert-butylsalicylidene)-1,2-diphenylethylenediamino cobalt (III) bromide [(R,R)-(salen-5)CoBr]: [(R,R)-(salen-5)Co] (0.25 g, 0.36 mmol) and p-toluenesulfonic acid monohydrate (68 mg, 0.36 mmol) were added to a 50 mL round bottomed flask charged with a Teflon stir bar. Methylene chloride (10 mL) was added to the reaction mixture and stirred for 2 h open to air at 22° C. The solvent was removed by rotary evaporation at 22° C., and the crude solid was washed with pentane (100 mL) and filtered. The crude material was dissolved in methylene chloride (25 mL) and added to a 125 mL separatory funnel. The organic layer was rinsed with saturated aqueous NaBr (3×25 mL). The organic layer was dried over Na$_2$SO$_4$ and evaporated under reduced pressure. The solid was washed with pentane (100 mL) and filtered to afford (R,R)-(salen-5)CoBr (0.12 g, 43%). $^1$H NMR (DMSO-d$_6$, 500 MHz): δ 1.22 (s, 1H), 1.76 (s, 18H), 5.62 (s, 2H), 6.97 (s, 2H), 7.23 (s, 2H), 7.41-7.48 (m, 12H). $^{13}$C NMR (DMSO-d$_6$, 125 MHz): δ 30.37, 31.35, 33.31, 35.73, 76.61, 117.64, 128.48, 129.18, 129.90, 134.93, 136.07, 142.02, 162.31, 166.50. HRMS (EI) m/z calcd. (C$_{44}$H$_{54}$BrCoN$_2$O$_2$—Br) 701.3517. found 701.3502.

Working Example XVII

Application of [PPN]Cl, [PPh$_4$]Cl, [PPh$_4$Br], [NBu$_4$Cl]

Bis(triphenylphosphine)iminium chloride ([PPN]Cl), tetraphenylphosphonium chloride [PPh$_4$Cl], tetraphenylphosphonium chloride [PPh$_4$Cl] were purchased from commercial sources and recrystallized from dry methylene chloride and diethyl ether under nitrogen before use. Tetrabutylammonium chloride [NBu$_4$]Cl was purchased from commercial sources and used as received. The synthesis of bis(triphenylphosphine)iminium tetraphenyl borate [PPN][BPh$_4$] is described in Reibenspies, J. H. *Z. Kristallogr.* 1994, 209, 620-621. Prakash, H.; Sisler, H. H. *Inorg. Chem.* 1968, 7, 2200-2203.

Working Example XIX

Synthesis of [PPN][OBzF$_5$]

Synthesis of bis(triphenylphosphine)iminium pentafluorobenzoate ([PPN][OBzF$_5$]): NaOH (0.19 g, 4.7 mmol) and pentafluorobenzoic acid (1.0 g, 4.7 mmol) were added to a 50 mL round-bottomed flask charged with a Teflon stir bar. Distilled H$_2$O (20 mL) was added to the reaction mixture, and it was stirred until all was dissolved. The solution was added to a 250 mL separatory funnel along with [PPN]Cl (0.40 g, 0.70 mmol) and methylene chloride (40 mL), and the mixture was shaken vigorously for 10 min. The organic layer was collected and dried by rotary evaporation to yield crude [PPN][OBzF$_5$] in quantitative yield. Precipitation from dry methylene chloride and diethyl ether under N$_2$ at −20° C. afforded a white powder (0.35 g, 67%). $^1$H NMR (CDCl$_3$, 500 MHz): δ67.39-7.46 (m, 24H), 7.60-7.63 (m, 6H). $^{13}$C NMR (CDCl$_3$, 125 MHz): δ116.93, 126.91 (dd, $^1J_{P-C}$=108.0 Hz, $^3J_{P-C}$=1.5 Hz), 129.55 (m), 132.02 (m), 133.88, 137.07 (d of m, $^1J_{F-C}$=255.5 Hz), 139.92 (d of m, $^1J_{F-C}$=250.3 Hz), 143.24 (d of m, $^1J_{F-C}$=247.3 Hz), 161.21. $^{19}$F NMR (470 MHz, CDCl$_3$): δ-164.64 (m), -159.92 (broad s), -142.52 (m). Anal. Calcd for $C_{43}H_{30}F_5NO_2P_2$: C, 68.89; H, 4.03; N, 1.87. Found: C, 69.07; H, 3.95; N, 1.83.

Working Example XX

Copolymers Made Using [(R,R)-(salen-1)CoI] and [(R,R)-(salen-1)CoOAc]

Copolymerizations were carried out with conditions and results set forth in Table 2 below:

TABLE 2

| Entry | Complex | Reaction Conditions | Time (h) | Yield[b] (%) | TOF[c] (h$^{-1}$) | Theoretical $M_n^d$ (kg/mol) | $M_n^e$ (kg/mol) | $M_w/M_n^e$ | Head-to-Tail Linkages[f] (%) |
|---|---|---|---|---|---|---|---|---|---|
| 1 | [(R,R)-(salen-1)CoI] | air-free | 5 | 43 | 43 | 21.9 | 19.6 | 1.15 | 79 |
| 2 | (R,R)-(salen-1)CoI | ambient | 5 | 37 | 37 | 18.9 | 9.5 | 1.33 | 81 |
| 3 | (R,R)-(salen-1)CoOAc | air-free | 2 | 30 | 74 | 15.1 | 15.5 | 1.16 | 83 |
| 4 | (R,R)-(salen-1)CoOAc | ambient | 2 | 25 | 62 | 12.7 | 10.4 | 1.31 | 83 |

[a]Polymerizations run in neat rac-propylene oxide (PO) with [PO]/[Co] = 500:1 at 22° C. with 800 psi of $CO_2$. Selectivity for poly(propylene carbonate) (PPC) over propylene carbonate was >99% in all cases. All product PPC contains ≥96% carbonate linkages as determined by $^1$H NMR spectroscopy.
[b]Based on isolated polymer yield.
[c]Turnover frequency (TOF) = mol PO · mol Co$^{-1}$ · h$^{-1}$.
[d]Theoretical number average molecular weight ($M_n$) = TOF · h · 102 g/mol.
[e]Determined by gel permeation chromatography calibrated with polystyrene standards in THF.
[f]Determined by $^{13}$C NMR spectroscopy As shown in Table 2, the runs in an inert atmosphere (entries 1 and 3) gave higher $M_n$ and lower PDI than the same reactions carried out in air (entries 2 and 4).

Working Example XXI

Copolymerizations Using [(R,R)-(salen-1)CoI], [(R,R)-(salen-1)CoBr], [(R,R)-(salen-1)CoCl], [(R,R)-(salen-1)CoOAc] and [(R,R)-(salen-1)CoOBzF$_5$]

Copolymerizations were carried out with conditions and results set forth in Table 3 below:

TABLE 3

| Entry | Complex | Yield[b] (%) | TOF[c] (h$^{-1}$) | $M_n^d$ (kg/mol) | $M_w/M_n^d$ | Head-to-Tail Linkages[e] (%) |
|---|---|---|---|---|---|---|
| 1 | [(R,R)-(salen-1)CoOAc] | 30 | 75 | 15.5 | 1.16 | 83 |
| 2 | [(R,R)-(salen-1)CoBzF$_5$] | 32 | 80 | 14.1 | 1.22 | 82 |
| 3 | [(R,R)-(salen-1)CoCl] | 26 | 65 | 13.4 | 1.19 | 82 |
| 4 | [(R,R)-(salen-1)CoBr] | 36 | 90 | 21.0 | 1.14 | 82 |
| 5 | [(R,R)-(salen-1)CoI] | 13 | 32 | 10.4 | 1.17 | 85 |
| 6 | [(R,R)-(salen-1)CoI] + [(R,R)-(salen-1)CoBr] (50:1) | 28 | 70 | 16.2 | 1.24 | 81 |

[a]Polymerizations run in neat rac-propylene oxide (PO) with [PO]/[Co] = 500:1 at 22° C. with 800 psi of $CO_2$ for 2 h. Selectivity for poly(propylene carbonate) (PPC) over propylene carbonate was >99% in all cases. All product PPC contains ≥92% carbonate linkages as determined by $^1$H NMR spectroscopy.
[b]Based on isolated polymer yield.
[c]Turnover frequency (TOF) = mol PO · mol Co$^{-1}$ · h$^{-1}$.
[d]Determined by gel permeation chromatography calibrated with polystyrene standards in THF.
[e]Determined by $^{13}$C NMR spectroscopy.
[OBzF$_5$] = pentafluorobenzoate.

As shown in Table 3, all the initiating groups tested, gave high molecular weight polycarbonate with narrow molecular weight distributions. Complex [(R,R)-(salen-1)CoI] provided the lowest TOF whereas complex [(R,R)-(salen-1)CoBr] provided the highest TOF.

Working Example XXII

Using [(R,R)-(salen-1)CoBr] and Varying Reaction Conditions

Copolymerizations were carried out with conditions and results set forth in Table 4 below:

TABLE 4

| entry | time (h) | yield (%) | TOF[b] (h$^{-1}$) | selectivity[c] (% PPC) | carbonate linkages[c] (%) | $M_n^d$ (kg/mol) | PDI | head to tail[e] (%) |
|---|---|---|---|---|---|---|---|---|
| 1 | 1 | 20% | 99 | >99:1 | 98% | 12.6 | 1.07 | 82% |
| 2 | 2 | 36% | 89 | >99:1 | 97% | 21.0 | 1.14 | 82% |
| 3 | 3 | 38% | 62 | >99:1 | 97% | 20.2 | 1.15 | 81% |
| 4[f] | 8 | 19% | 47 | >99:1 | 97% | 16.6 | 1.18 | 81% |

TABLE 4-continued

| entry | time (h) | yield (%) | TOF[b] ($h^{-1}$) | selectivity[c] (% PPC) | carbonate linkages[c] (%) | $M_n^d$ (kg/mol) | PDI | head to tail[e] (%) |
|---|---|---|---|---|---|---|---|---|
| 5[g] | 10 | 12% | 6 | >99:1 | 91% | 7.2 | 1.15 | 85% |
| 6[h] | 2 | 49% | 121 | >99:1 |  | 20.1 | 1.21 |  |

Reaction conditions: 800 psi $CO_2$, 22° C., 1 mL of neat rac-PO, [PO]/[Co] = 500.
[b]Turnover frequency = (mol PO/(mol Zn · h)).
[c]Determined by $^1$H NMR spectroscopy.
[d]Determined by gel permeation chromatography in tetrahydrofuran at 40° C. relative to polystyrene standards.
[e]Determined by $^{13}$C NMR spectroscopy.
[f][PO]/[Co] = 2000.
[g]0° C.
[h]S-PO was used instead of rac-PO.

As shown in Table 4, increasing the time of polymerization increases molecular weight while slightly decreasing activities (entries 1-3) while more dilute reaction conditions decrease the catalyst activity (entry 4) as does lowering the reaction temperature to 0° C. (entry 5). As indicated by comparison of entries 2 and 6, the activity is enhanced if enantiomerically pure S—PO is used instead of racemic PO.

Working Example XXIII

Effect of Change of Catalyst Backbone on Copolymerizations

Copolymerizations were carried out with conditions and results set forth in Table 5 below:

TABLE 5

| Entry | Catalyst | Yield (%)[b] | TOF ($h^{-1}$)[c] | Carbonate Linkages (%)[d] | $M_n$ (kg/mol)[e] | $M_w/M_n$[e] | Head-to-Tail Linkages (%)[f] |
|---|---|---|---|---|---|---|---|
| 1 | [(R,R)-(salen-1)CoBr] | 38 | 63 | 97 | 20.2 | 1.15 | 81 |
| 2 | [(R)-(salen-2)CoBr] | 32 | 53 | 97 | 13.9 | 1.18 | 82 |
| 3[g] | [(salen-3)CoBr] | 0 | 0 | NA | NA | NA | NA |
| 4 | [(salen-4)CoBr] | 38 | 63 | >99 | 21.1 | 1.16 | 85 |
| 5 | [(R,R)-(salen-5)CoBr] | 12 | 20 | 99 | 10.1 | 1.14 | 76 |
| 6 | [(salen-6)CoBr] | 14 | 23 | 89 | 11.3 | 1.29 | 79 |
| 7 | [(R,R)-(salen-7)CoBr] | 33 | 55 | 96 | 15.2 | 1.13 | 76 |
| 8 | [(R,R)-(salen-8)CoBr] | 43 | 72 | 94 | 35.8 | 1.15 | 70 |
| 9[g] | [(R,R)-(salen-9)CoBr] | 0 | 0 | NA | NA | NA | NA |
| 10 | [(R,R)-(salen-10)CoBr] | 8 | 13 | 69 | 4.5 | 1.12 | 80 |
| 11 | [(R,R)-(salen-11)CoBr] | 11 | 18 | >99 | 9.1 | 1.13 | 89 |

[a]Copolymerizations were run in neat rac-propylene oxide (PO) with [PO]:[Co] = 500:1 at 22° C. with 800 psi of $CO_2$ for 3 h. Selectivity for poly(propylene carbonate) (PPC) over propylene carbonate was >99:1 for entries 1-10, and 97:3 for entry 11.
[b]Based on isolated PPC yield.
[c]Turnover frequency for PPC (mol PO · (mol Co)$^{-1}$ · h$^{-1}$).
[d]Determined by $^1$H NMR spectroscopy.
[e]Determined by GPC.
[f]Determined by $^{13}$C NMR spectroscopy.
[g]Entries 1 and 4 produced the best results.

Entries 1 and 4 produced the best results.

Working Example XIV

Effect of Different Relative Levels of PPNCl Co-Catalyst on Copolymerization Results Copolymerizations were carried out with variations and results as set forth in Tables 6 and 7 below:

TABLE 6

| Entry | Complex | Yield (%)[b] | TOF ($h^{-1}$)[c] | Selectivity (% PPC)[d] | $M_n$ (kg/mol)[e] | $M_w/M_n$[e] | Head-to-Tail Linkages (%)[f] |
|---|---|---|---|---|---|---|---|
| 1 | [(R,R)-(salen-1)CoOAc] | 11 | 110 | 86 | 7.9 | 1.15 | 93 |
| 2 | [(R,R)-(salen-1)CoOBzF$_5$] | 52 | 520 | >99 | 43.0 | 1.10 | 93 |

TABLE 6-continued

| Entry | Complex | Yield[b] (%) | TOF[c] (h$^{-1}$) | Selectivity[d] (% PPC) | $M_n$[e] (kg/mol) | $M_w/M_n$[e] | Head-to-Tail Linkages[f] (%) |
|---|---|---|---|---|---|---|---|
| 3 | [(R,R)-(salen-1)CoCl] | 43 | 430 | >99 | 35.4 | 1.09 | 95 |
| 4 | [(R,R)-(salen-1)CoBr] | 46 | 460 | 89 | 33.2 | 1.09 | 95 |

[a] Polymerizations run in neat rac-propylene oxide (PO) with [PO]:[[PPN]Cl]:[Co] = 2000:1:1 at 22° C. with 200 psi of $CO_2$ for 2 h. All product poly(propylene carbonate) (PPC) contains ≧98% carbonate linkages as determined by $^1$H NMR spectroscopy.
[b] Based on isolated polymer yield.
[c] Turnover frequency = mol PO · mol Co$^{-1}$ · h$^{-1}$.
[d] Selectivity for PPC over propylene carbonate.
[e] Determined by gel permeation chromatography calibrated with polystyrene standards in THF.
[f] Determined by $^{13}$C NMR spectroscopy.
[PPN] = bis (triphenylphosphine)iminium.
[OBzF$_5$] = pentafluorobenzoate.

TABLE 7

| Entry | PO:[PPN]Cl:[(R,R)-(salen-1)CoOBzF$_5$] | Time (h) | Yield[b] (%) | TOF[c] (h$^{-1}$) | Selectivity[d] (% PPC) | $M_n$[e] (kg/mol) | $M_w/M_n$[e] | Head-to-Tail Linkages[f] (%) |
|---|---|---|---|---|---|---|---|---|
| 1 | 2000:1:1 | 1 | 31 | 640 | 99 | 26.8 | 1.13 | 94 |
| 2 | 2000:1:1 | 2 | 52 | 520 | >99 | 43.0 | 1.10 | 93 |
| 3 | 2000:1:1 | 6 | 59 | 200 | 56 | 41.4 | 1.36 | 93 |
| 4 | 2000:2:1 | 2 | 53 | 530 | 97 | 33.9 | 1.08 | 93 |
| 5 | 2000:0.5:1 | 2 | 36 | 360 | >99 | 46.3 | 1.07 | 94 |

[a] Polymerizations run in neat rac-propylene oxide (PO) at 22° C. with 200 psi of $CO_2$. All product poly(propylene carbonate) (PPC) contains ≧98% carbonate linkages as determined by $^1$H NMR spectroscopy.
[b] Based on isolated polymer yield.
[c] Turnover frequency = mol PO · mol Co$^{-1}$ · h$^{-1}$.
[d] Selectivity for PPC over propylene carbonate.
[e] Determined by gel permeation chromatography calibrated with polystyrene standards in THF.
[f] Determined by $^{13}$C NMR spectroscopy.
[PPN] = bis(triphenylphosphine)iminium.
[OBzF$_5$] = pentafluorobenzoate

Working Example XXV

Effect of Cocatalyst

Copolymerizations were carried out with variations in catalyst and co-catalyst with results as set forth in Table 8 below:

Working Example XXVI

Copolymerization at 10 psi of $CO_2$

The [(R,R)-(salen-1)CoOBzF$_5$/[PPN]Cl catalyzed PO/CO$_2$ copolymerization carried out at 10 psi resulted in a TOF of 160 h$^{-1}$, affording 32% yield of PPC.

TABLE 8

| Entry[a] | Cocatalyst | Time (h) | Yield (%)[b] | TOF (h$^{-1}$)[c] | Selectivity PPC:PC[d] | $M_n$ (kg/mol) | $M_w/M_n$ | Head-to-Tail Linkages (%) |
|---|---|---|---|---|---|---|---|---|
| 1 | None | 24 | trace | NA | NA | NA | NA | NA |
| 2 | [PPN][BPh$_4$] | 24 | trace | NA | NA | NA | NA | NA |
| 3 | [PPN]Cl | 0.5 | 30 | 600 | 99:1 | 9.8 | 1.18 | 94 |
| 4 | [PPN][OBzF$_5$] | 0.5 | 36 | 720 | >99:1 | 15.9 | 1.16 | 94 |
| 5 | [PPh$_4$]Br | 0.5 | 24 | 480 | 96:4 | | | |
| 6 | [PPh$_4$]Cl | 0.5 | 25 | 550 | 97:3 | 8.6 | 1.19 | 94 |
| 7 | [n-Bu$_4$N]Cl | 2 | 29 | 150 | >99:1 | 6.6 | 1.15 | 93 |
| 8 | N(CH$_2$CH$_3$)$_3$ | 2 | 38 | 190 | >99:1 | 18.5 | 1.17 | |
| 9 | N((CH$_2$)$_7$CH$_3$)$_3$ | 2 | 35 | 175 | >99:1 | 18.1 | 1.14 | 93 |

[a] Polymerizations run with catalyst [(R,R)-(salen-1)CoOBzF$_5$] in neat rac-PO with [PO]:[Co]:[cocatalyst] = 1000:1:1 at 22° C. with 100 psi of CO$_2$.
[b] based on isolated PPC yield.
[c] TOF for PPC.
[d] Selectivity for PPC over PC.
[e] [PO]:[Co]:[cocatalyst] = 2000:1:1.
[f] [PO]:[Co]:[cocatalyst] = 500:1:1.

Working Example XXVII

Use of R₁ Substituted Ethylene Oxides in the Copolymerization Using [(R,R)-(salen-1)CoOOBzF₅]/[PPN]Cl

TABLE 9

| Entry | $R_1$ | Time (h) | Yield[b] (%) | Polymer:Cyclic[c] | TOF[d] ($h^{-1}$) | Carbonate Linkages[e] (%) | $M_n$[f] (kg/mol) | $M_w/M_n$[f] | Head-to-Tail Linkages[g] (%) |
|---|---|---|---|---|---|---|---|---|---|
| 1 | $CH_2OCH_3$ | 6 | 56 | 85:15 | 93 | | 4.7 | 1.42 | |
| 2 | $CH_2OPh$ | 8 | 40 | 92:8 | 50 | | 13.1 | 1.19 | |
| 3 | $CH_2OSi^tBu(CH_3)_2$ | 50 | 90 | 81:19 | 2 | | 45.4 | 1.15 | 87 |
| 4[h] | $CH=CH_2$ | 48 | 58 | 91:9 | 24 | >99 | 44.8 | 1.15 | 52 |
| 5[i] | $CH_2CH_3$ | 2 | 39 | 95:5 | 194 | 98 | 24.1 | 1.15 | >99 |
| 6 | $CH_2CH_2CH_2CH_3$ | 6 | 58 | 74:26 | 97 | 94 | 20.7 | 1.22 | |
| 7 | H | 2 | 80 | 99:1 | 400 | 80 | 32.1 | 1.18 | NA |

[a]All reactions were performed in neat rac-epoxide with catalyst [(R,R)-(salen-1)CoOOBzF₅] and cocatalyst [PPN]Cl with [epoxide]:[Co]:[[PPN]Cl] = 1000:1:1 at 22° C. with 100 psi of CO₂ unless otherwise noted.
[b]Based on total polymer + cyclic carbonate.

VARIATIONS

The foregoing description of the invention has been presented describing certain operable and preferred embodiments. It is not intended that the invention should be so limited since variations and modifications thereof will be obvious to the skilled in the art, all of which are within the spirit and scope of the invention.

What is claimed is:

1. A catalyst system comprising as a catalyst

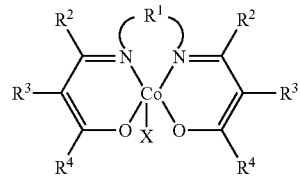

(I)

where R¹ is a hydrocarbon bridge which may be substituted with $C_1$-$C_{20}$ alkyl, $C_1$-$C_{20}$ alkoxy, halogen, nitro, cyano or amine;

where R², R³ and R⁴ are the same or different and are selected from the group consisting of H, $C_1$-$C_{20}$ alkyl, $C_6$-$C_{20}$ aryl, and $C_1$-$C_{20}$ fluorocarbon and where R¹ and R² or R² and R³ or R³ and R⁴ can form a ring which are substituted with H, $C_1$-$C_{20}$ alkyl, $C_6$-$C_{20}$ aryl, $C_1$-$C_{20}$ alkyl, $C_6$-$C_{20}$ aryl substituted with $C_1$-$C_{20}$ alkyl, $C_1$-$C_{20}$ alkoxy, phenoxy, $C_1$-$C_{20}$ carboxylate, $C_1$-$C_{20}$ acyl, amino, $C_1$-$C_{20}$ fluoroalkyl, cyano, nitro and halogen; and where X is any nucleophile which can ring open an epoxide;

and as a cocatalyst a salt where the salt cation has the structural formula: $[R_3P=N=PR_3]^+$ where R is selected from the group consisting of $C_1$-$C_{20}$ alkyl, $C_6$-$C_{20}$ aryl, and a solid support, the salt anion is a nucleophile which can ring open an epoxide, and the R groups are the same or different.

2. The catalyst system of claim 1 where the salt cation has the structure

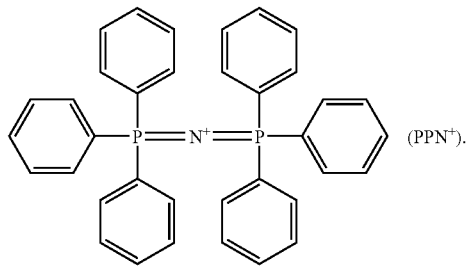

3. The catalyst system of claim 1 where in formula I, the

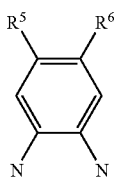

moiety is:

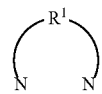

where R⁵ and R⁶ are the same or different and are H, $C_1$-$C_{20}$ alkyl, $C_6$-$C_{20}$ aryl, halogen, nitro, cyano, $C_1$-$C_{20}$ alkoxy, or amine.

4. The catalyst system of claim 1 where in formula I, the moiety is:

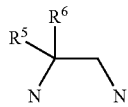

where R⁵ and R⁶ are the same or different and are selected from the group consisting of: —H, $C_1$-$C_{20}$ alkyl, $C_6$-$C_{20}$ aryl, halogen, nitro, cyano, $C_1$-$C_{20}$ alkoxy, and amine.

5. The catalyst system of claim 4 where $R^5$ and $R^6$ are each $C_{1\text{-}20}$ alkyl.

6. The catalyst system of claim 5 where $R^5$ and $R^6$ are each —$CH_3$.

7. The catalyst system of claim 5 where $R^2$ is hydrogen and $R^3$ and $R^4$ form a phenyl ring substituted with $C_{1\text{-}20}$ alkyl.

8. The catalyst system of claim 1 where the catalyst has the formula:

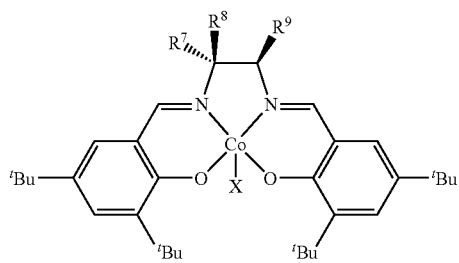

where $R^7$ is Me, $R^8$ is Me, and $R^9$ is H.

9. The catalyst system of claim 8 where X is Br.

10. The catalyst system of claim 1 where in formula I, the

moiety is:

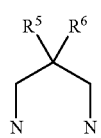

where $R^5$ and $R^6$ are the same or different and are selected from the group consisting of: —H, $C_1$-$C_{20}$ alkyl, $C_6$-$C_{20}$ aryl, halogen, nitro, cyano, $C_1$-$C_{20}$ alkoxy, and amine.

11. The catalyst system of claim 1 where in formula I, the

moiety is:

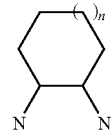

where n is 0 or 1.

12. The catalyst system of claim 11, where the

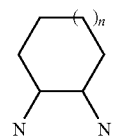

moiety is racemic.

13. The catalyst system of claim 11, where the

moiety has (S,S) stereochemistry.

14. The catalyst system of claim 11, where the

moiety has (R,R) stereochemistry.

15. The catalyst system of claim 11, where n is 1.

16. The catalyst system of claim 1 where X is selected from the group consisting of: halogen, $C_1$-$C_{20}$ alkyl, $C_1$-$C_{20}$ amido, cyano, azide, $C_1$-$C_{20}$ alkyl carboxylate, $C_6$-$C_{20}$ aryl carboxylate, $C_1$-$C_{20}$ alkoxide and phenoxide.

17. The catalyst system of claim 1 where X is selected from the group consisting of: —Cl; —Br; —I; acetate; 2,3,4,5,6-pentafluorobenzoate; and p-trifluoromethylbenzoate.

18. The catalyst system of claim 1, where $R^3$ and $R^4$ form phenyl rings.

19. The catalyst system of claim 18, where the phenyl rings formed by $R^3$ and $R^4$ have substituents selected from the group consisting of: $C_1$-$C_{20}$ alkyl, $C_6$-$C_{20}$ aryl, $C_6$-$C_{20}$ aryl substituted with $C_1$-$C_{20}$ alkyl, $C_1$-$C_{20}$ alkoxy, phenoxy, $C_1$-$C_{20}$ carboxylate, $C_1$-$C_{20}$ acyl, amino, $C_1$-$C_{20}$ fluoroalkyl, cyano, nitro, cyano, and halogen.

20. The catalyst system of claim 1, where the catalyst has the structure:

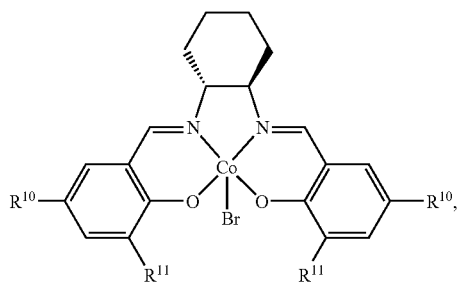

where when $R^{11}$ is -$^tBu$, $R^{10}$ is —H, —Br, or —OMe; when $R^{11}$ is —H, $R^{10}$ is -$^tBu$; when $R^{11}$ is -Me, $R^{10}$ is —H; or when $R^{11}$ is —CPh(CH$_3$)$_2$, $R^{10}$ is —CPh(CH$_3$)$_2$.

21. The catalyst system of claim 20 where $R^{10}$ and $R^{11}$ are —CPh(CH$_3$)$_2$.

22. The catalyst system of claim 1, where the catalyst has the structural formula:

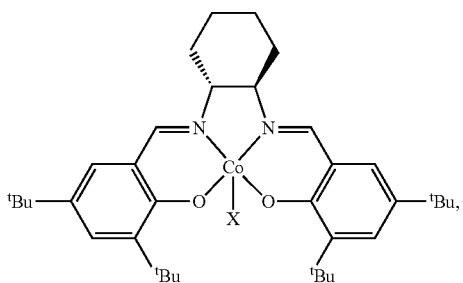

where X is selected from the group consisting of: halogen, $C_1$-$C_{20}$ alkyl, $C_1$-$C_{20}$ amido, cyano, azide, $C_1$-$C_{20}$ alkyl carboxylate, $C_6$-$C_{20}$ aryl carboxylate, $C_1$-$C_{20}$ alkoxide and phenoxide.

23. The catalyst system of claim 22, where X is selected from the group consisting of: halogen, $C_1$-$C_{20}$ alkyl carboxylate and $C_6$-$C_{20}$ aryl carboxylate.

24. The catalyst system of claim 22, where X is selected from Br, Cl, I, OAc, OBzCF$_3$, or OBzF$_5$, where OBzCF$_3$ is p-trifluoromethylbenzoate and OBzF$_5$ is 2,3,4,5,6-pentafluorobenzoate.

25. The catalyst system of claim 2, where the salt anion is selected from the group consisting of Cl and OBzF$_5$, where OBzF$_5$ is 2,3,4,5,6-pentafluorobenzoate.

26. The catalyst system of claim 1, where the catalyst has the structural formula:

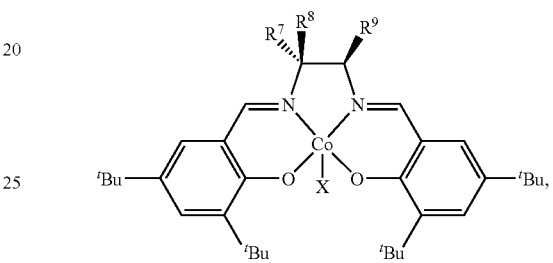

where $R^7$ is Me, $R^8$ is Me, $R^9$ is H, and X is selected from the group consisting of: halogen, $C_1$-$C_{20}$ alkyl, $C_1$-$C_{20}$ amido, cyano, azide, $C_1$-$C_{20}$ alkyl carboxylate, $C_6$-$C_{20}$ aryl carboxylate, $C_1$-$C_{20}$ alkoxide and phenoxide.

27. The catalyst system of claim 26, where X is Br.

28. The catalyst system of claim 1, where X is not O$_2$CCl$_3$ or a nitrophenol when $R^1$ is 1,2-cyclohexanediyl.

* * * * *